US011980428B2

United States Patent
Siccardi et al.

(10) Patent No.: US 11,980,428 B2
(45) Date of Patent: May 14, 2024

(54) METHOD OBTAINED BY MEANS OF COMPUTER FOR CHECKING THE CORRECT ALIGNMENT OF A HIP PROSTHESIS AND A SYSTEM FOR IMPLEMENTING SAID CHECK

(71) Applicant: MEDACTA INTERNATIONAL SA, Castel San Pietro (CH)

(72) Inventors: Francesco Siccardi, Castel San Pietro (CH); Massimiliano Bernardoni, Castel San Pietro (CH); Daniele Ascani, Castel San Pietro (CH)

(73) Assignee: Medacta International SA, Castel San Pietro (CH)

( * ) Notice: Subject to any disclaimer, the term of this patent is extended or adjusted under 35 U.S.C. 154(b) by 333 days.

(21) Appl. No.: 17/602,215

(22) PCT Filed: Apr. 6, 2020

(86) PCT No.: PCT/IB2020/053257
§ 371 (c)(1),
(2) Date: Oct. 7, 2021

(87) PCT Pub. No.: WO2020/208495
PCT Pub. Date: Oct. 15, 2020

(65) Prior Publication Data
US 2022/0192755 A1  Jun. 23, 2022

(30) Foreign Application Priority Data
Apr. 8, 2019  (IT) .......................... 102019000005350

(51) Int. Cl.
*A61B 34/20* (2016.01)
*A61B 90/00* (2016.01)
(Continued)

(52) U.S. Cl.
CPC ................ *A61B 34/20* (2016.02); *A61F 2/32* (2013.01); *G06T 7/0016* (2013.01); *G06T 7/344* (2017.01);
(Continued)

(58) Field of Classification Search
None
See application file for complete search history.

(56) References Cited

U.S. PATENT DOCUMENTS

2017/0258526 A1    9/2017  Lang
2018/0150929 A1 *  5/2018  Pheiffer .................... G06T 7/30

FOREIGN PATENT DOCUMENTS

JP          2018079304 A        5/2018

OTHER PUBLICATIONS

Penney, Graeme P., et al. "Postoperative Calculation of Acetabular Cup Position Using 2-D-3-D Registration," IEEE Transactions on Biomedical Engineering, vol. 54, No. 7 (Jul. 2007); pp. 1342-1348.

(Continued)

*Primary Examiner* — Kee M Tung
*Assistant Examiner* — Jed-Justin Imperial
(74) *Attorney, Agent, or Firm* — Meunier Carlin & Curfman LLC (57) ABSTRACT

A computer-implemented method for checking the correct alignment of a hip prosthesis, includes: detecting a 3D model of the pelvic bone of a patient in a preoperative phase, detecting at least one 2D image of the pelvic bone in post-implant situation, selecting an image of the 3D model according to a first inclination thereof and detecting a reference element on said selected image of the 3D model, identifying a plurality of reference points on the 2D image, superimposing the 2D image on said selected image of the 3D model, checking the correct superimposition and correspondence of the reference points of the 2D image with the (Continued)

reference element with said image of the 3D model, and detecting possible differences in the positioning of the pelvic bone in post-implant configuration with respect to the pre-operative situation.

15 Claims, 5 Drawing Sheets

(51) Int. Cl.
  *A61F 2/32* (2006.01)
  *G06T 7/00* (2017.01)
  *G06T 7/33* (2017.01)
  *G06T 7/68* (2017.01)
  *G06T 19/20* (2011.01)
(52) U.S. Cl.
  CPC ............... *G06T 7/68* (2017.01); *G06T 19/20* (2013.01); *A61B 2034/2065* (2016.02); *A61B 2090/364* (2016.02); *G06T 2207/30008* (2013.01); *G06T 2207/30052* (2013.01); *G06T 2207/30168* (2013.01); *G06T 2210/41* (2013.01); *G06T 2219/2004* (2013.01)

(56) References Cited

OTHER PUBLICATIONS

International Search Report and Written Opinion issued in PCT/IB2020/053257, dated Aug. 13, 2020, 15 pages.
English Translation of Notice of Reasons of Refusal in JP 2021-559391, dated Sep. 8, 2022, 9 pages.

\* cited by examiner

METHOD OBTAINED BY MEANS OF COMPUTER FOR CHECKING THE CORRECT ALIGNMENT OF A HIP PROSTHESIS AND A SYSTEM FOR IMPLEMENTING SAID CHECK

TECHNICAL FIELD

This invention relates to a method, obtained by means of computer, for checking the correct alignment of a hip prosthesis.

In addition, this invention relates to a system for checking the correct alignment of a hip prosthesis.

Specifically, this method is used to check the correct alignment of the hip prosthesis in intraoperative or postoperative situations.

Specifically, following the implant of a hip prosthesis, which involves the insertion of a femoral stem and a femoral head to be inserted inside the acetabular cup, the position of the leg in relation to the pelvic bone may undergo displacements or inclinations that no longer correspond to the patient's natural anatomy.

Specifically, depending on the reciprocal position between the femoral head and stem, there may be a lengthening or shortening of the leg and a lateral displacement (or offset) of the leg itself in relation to the patient's sagittal axis.

Two other parameters that are critical in checking the correct positioning of the acetabular cup are the inclination and anteversion of the acetabular cup. The incorrect positioning of the acetabular cup, in terms of inclination and anteversion, could cause: 1) disarticulation of the femoral head from the cup itself causing a hip dislocation, 2) the femoral head overloads the plastic insert contained in the acetabular cup causing enough wear to lead to premature failure of the hip prosthesis, 3) inflammation of the surrounding soft tissue.

It is, therefore, important to recreate the preoperative anatomical conditions of the patient's hip after the implant.

When implanting or replacing a hip prosthesis, it is necessary to monitor whether the post-implant position, in terms of femur offset and lengthening and the inclination and anteversion of the acetabular cup, are close to the values established in the preoperative phase.

PRIOR ART

Currently, a methodology called 2D-2D is used to check that the postoperative hip and femur position is similar to the settings identified in the preoperative phase. This methodology is based on the comparison of two two-dimensional images, obtained with x-rays or fluoroscopies.

A preoperative x-ray of the patient is performed, a horizontal axis and a vertical axis (Cartesian system) are defined on this image that will serve as a reference to define the femur displacement in terms of lengthening (in relation to the vertical axis) and offset (in relation to the horizontal axis), and the inclination and anteversion of the acetabular cup (in relation to the horizontal axis). Subsequently, different reference points are identified and selected on the preoperative image, typically bone references, and on the post-implant image, typically the ellipse given by the edge of the acetabular cup.

Once the reference points have been identified, the preoperative and post-implant images are superimposed, taking the selected points as a reference.

Using the aligned positions, the change in leg length and the change in lateral offset can be estimated. The ellipse defined by the edge of the acetabular cup, which is manually marked by the user, determines the image scale, the implant size, and the orientation of the cup in relation to the camera.

The ellipse aspect ratio is used to calculate the anteversion of the acetabular cup. The orientation of the ellipse is used to calculate the inclination of the cup. The ellipse size and diameter given are used as a scale reference to convert the femur displacement from pixels to millimetres.

Initially, the two images are superimposed focusing on the part relating to the pelvic bone.

The user displaces the preoperative pelvic bone image so that it is aligned with the postoperative pelvic bone image. From the previously specified horizontal reference line and the rotation of the pelvis alignment, the horizontal reference line can be calculated in the postoperative image.

Following this, the user moves on to superimposing the femoral part of the two 2D images—preoperative and post-implant. It is possible that the abduction of the femur has changed, and this is evaluated by an algorithm using the rotation values of the pelvis and femur alignment.

After all inputs have been provided, it is possible to calculate the change in leg length, the change in lateral offset, and the orientation of the acetabular cup by means of mathematical formulas that involve calculating the angle between the slope of the trochanters.

To estimate the orientation of the acetabular cup in terms of anteversion and inclination, the ellipse that the user has previously drawn on the post-implant 2D image is used, by measuring the angle between the horizontal reference line and the ellipse axis and applying another mathematical formula.

The value obtained for the degree of anteversion of the acetabular cup, evaluated with the known 2D-2D method, is not accurate because the reference by which the anteversion is calculated is an estimate by the surgeon and is not a plane defined by a bone structure.

The value obtained is, therefore, subject to approximation errors that could lead to problems in the positioning of the prosthesis that could cause the patient problems.

The purpose of this invention is to propose a method, obtained by means of computer, for checking the correct alignment of a hip prosthesis that is free of the drawback found in the prior art.

The purpose of this invention is, therefore, to propose a method, obtained by computer, for checking the correct alignment of a hip prosthesis that gives more precise and accurate values related to the anteversion and inclination of the acetabular cup, in order to avoid margins of error that could be significant when the implant is completed.

Another purpose of this invention is to provide a system for checking the correct alignment of a hip prosthesis that is able to return anteversion and inclination values that are close to the preoperative ones and with the greatest possible precision and accuracy.

These and additional purposes and advantages are achieved with a method, obtained by means of a computer, for checking the correct alignment of a hip prosthesis according to what is described in the appended claims.

SUMMARY

A first aspect of this invention provides a method obtained by means of a computer for checking the correct alignment of a hip prosthesis, comprising the steps of detecting a 3D model of the pelvic bone of a patient in the preoperative phase; detecting at least one 2D image of the pelvic bone in the post-implant situation; selecting an image of the 3D model according to a first inclination thereof and detecting a reference element on said 3D image of a reference element; identifying a plurality of reference points on the 2D image; superimposing the 2D image on the selected image of the 3D model; checking the correct superimposition and correspondence of the reference points of the 2D image with the reference element with said image of the 3D model; generating a signal representative of a value of compliance with a predetermined superimposition criterion between the reference points of the 2D image and the reference element of the image of the 3D model. If the predetermined compliance value is above a predetermined error threshold, modifying the inclination of the 3D model and repeating the procedure. If said predetermined compliance value is below a predetermined error threshold, the image of the 3D model identified is correct and the superimposition and correspondence between the acetabular cup of the 3D model and the ellipse, given by the projection of the acetabular cup in 2D, is perfect and the user can proceed to detecting possible differences in the positioning of the pelvic bone in the post-implant configuration with respect to the preoperative situation as a function of the superimposition and correspondence of the reference points of the 2D image with the reference element of the image of the 3D model.

In addition, the method requires that the plurality of reference points on the 2D image is represented by the ellipse given by the projection of the edge of the acetabular cup and that the reference element on the image of the 3D model is represented by the acetabular cup.

The superimposition of the 2D image and of the image of the 3D model includes aligning the central symmetry axis of the acetabular cup with the axis passing through the centre of the ellipse given by the projection of the acetabular cup.

The method comprises, in addition, the step of modifying the inclination of the 3D model if this predetermined compliance value is above a predetermined error threshold; this compliance value occurring at the perfect superimposition and correspondence between the acetabular cup of the 3D model and the ellipse given by the 2D projection of the acetabular cup.

The method comprises, in addition, the step of detecting the possible anteversion and inclination of the post-implant acetabular cup in relation to the preoperative situation, as a function of the superimposition and correspondence of the reference points of the 2D image with the reference element of the image of the 3D model.

Preferably, the detection of the 3D model of the pelvic bone is carried out using preoperative tomography.

In a second aspect, this invention includes a system for checking the correct alignment of a hip prosthesis, comprising: a first detecting device adapted to detect a 3D model of the pelvic bone of a preoperative patient; a second detecting device adapted to detect at least one 2D image of the pelvic bone in a post-implant situation; a processing unit configured to acquire and process the 2D image and a selected image of the 3D model according to a first inclination comprising: a first identifying module configured to identify a reference element on the image of the 3D model; a second identifying module configured to identify a plurality of reference points on the 2D image; a superimposition module configured to superimpose the 2D image on the selected image of the 3D model; a checking module configured to check the correct superimposition and correspondence of the reference points of the 2D image with the reference element of the selected image of the 3D model; a signal generating module configured to generate a signal representative of a value of compliance with a predetermined superimposition criterion between the reference points of the 2D image and the reference element of the image of the 3D model; a detecting module configured to detect any differences in pelvic bone positioning in the post-implant configuration with respect to the preoperative situation as a function of the superimposition and correspondence of the reference points of the 2D image with the reference element of the selected image of the 3D model.

The first detecting device in the system is configured to detect a 3D model of the patient's pelvic bone using preoperative tomographies.

The processing unit also comprises a selecting module to select an image of the 3D model according to an initial inclination thereof.

In the first identifying module, the reference element is preferably represented by the acetabular cup.

In the second identifying module, the reference points are preferably represented by an ellipse given by the projection of the edge of the acetabular cup.

The superimposition module is configured to receive, from the first and second identifying modules, the 2D and 3D images on which the reference points and the reference element were identified, respectively, and to superimpose the 2D image with the selected image of the 3D model.

The checking module is configured to receive, from the superimposition module, the superimposed 2D and 3D images, and to check the correct superimposition and correspondence of the reference points of the 2D image with the reference element of the selected image of the 3D model. The checking module is configured to check that the alignment between the central symmetry axis of the acetabular cup and the axis passing through the centre of the ellipse given by the projection of the acetabular cup is close to a predetermined value of compliance with a predetermined superimposition criterion.

The signal generating module is configured to receive data related to the predetermined compliance value, and to generate a signal representative of the compliance value if there is the correct superimposition and correspondence of the reference points with the reference element.

The detecting module is configured to receive the signal from the signal generating module and, after having detected the possible anteversion and inclination of the acetabular cup in the post-implant configuration with respect to the preoperative situation, to return indicative numerical values of the anteversion and inclination of the post-implant acetabular cup with respect to the preoperative configuration.

BRIEF DESCRIPTION OF THE FIGURES

A method obtained by means of computer and a system for checking the correct alignment of a hip prosthesis as described and claimed is also illustrated in the following figures that are intended to be illustrative and not exhaustive, wherein:

DETAILED DESCRIPTION

With reference to the attached figures, the reference number 100 indicates a system for checking the correct alignment of a hip prosthesis.

Figure 1:
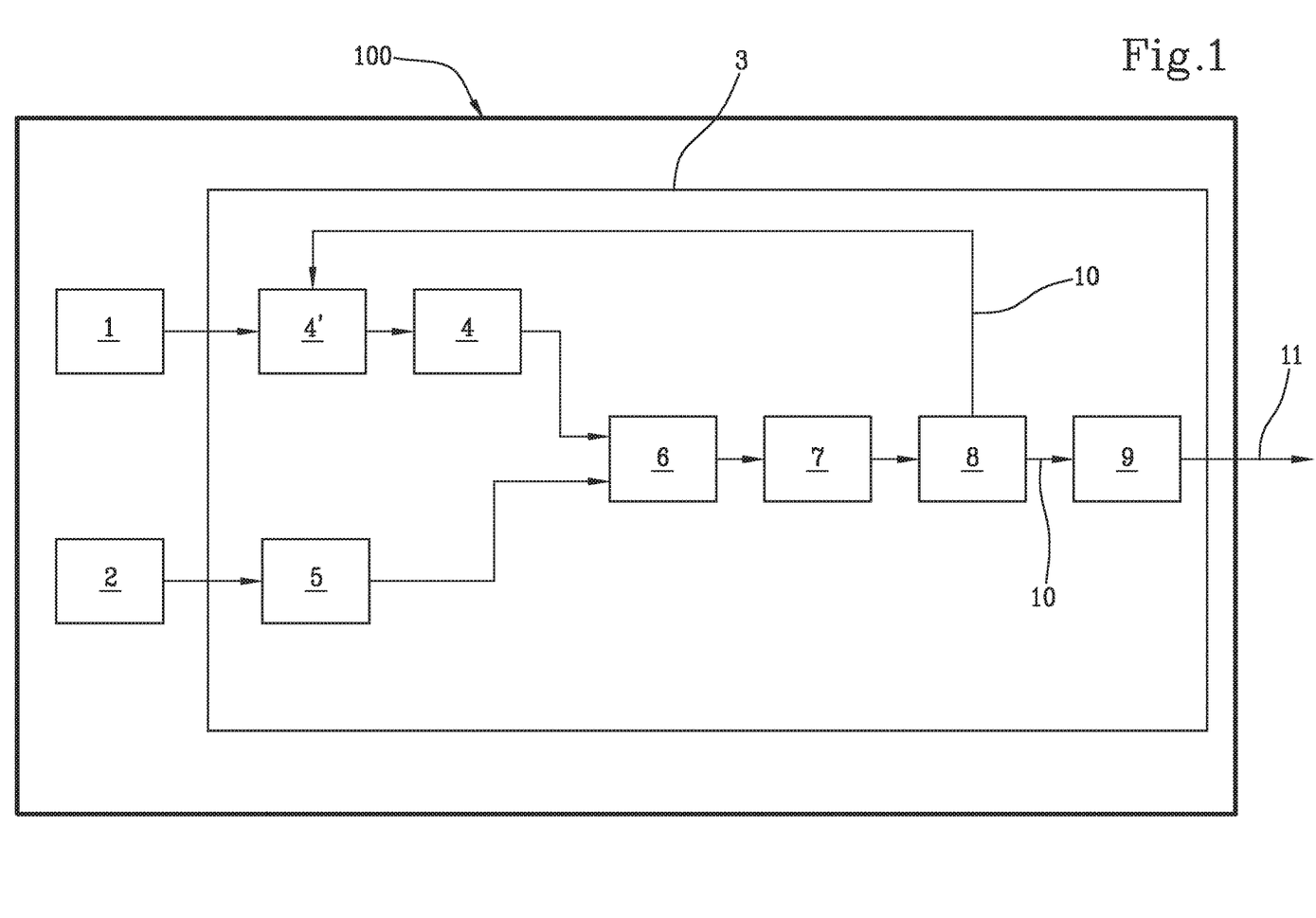
FIG. 1 is a block diagram of the method obtained by means of a computer for checking the correct alignment of a hip prosthesis, according to this invention, joined to a femoral bone and a hip.
Figure 9:
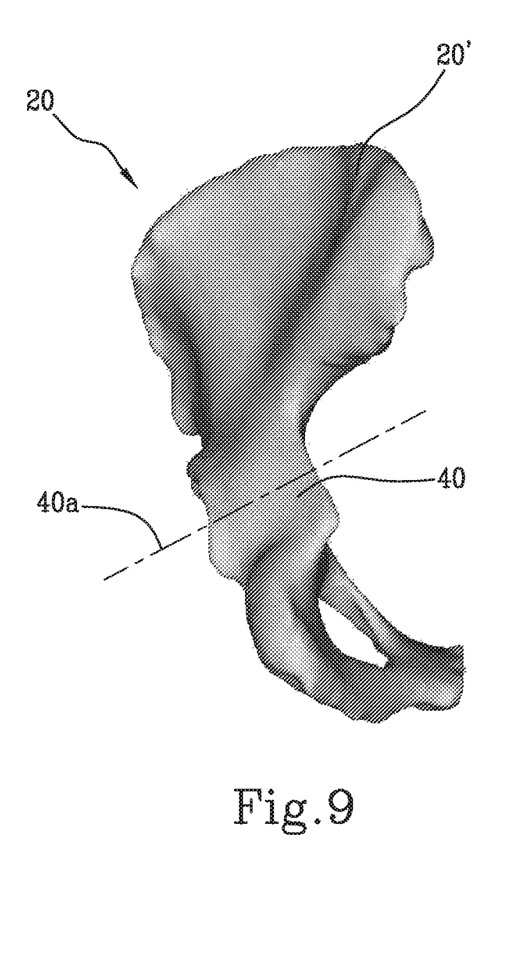
FIG. 9 is a selected image of the 3D model of the bone structure of the hip.

Considering the representative diagram in FIG. 1, the system 100 comprises a first detecting device 1 adapted to detect a 3D model 20 of a patient's pelvic bone 20' in a preoperative phase (FIG. 9). In other words, a three-dimensional model of the pelvic bone is detected, preferably by means of tomographies, in order to visualise the patient's bone before the operation.

Figure 5:
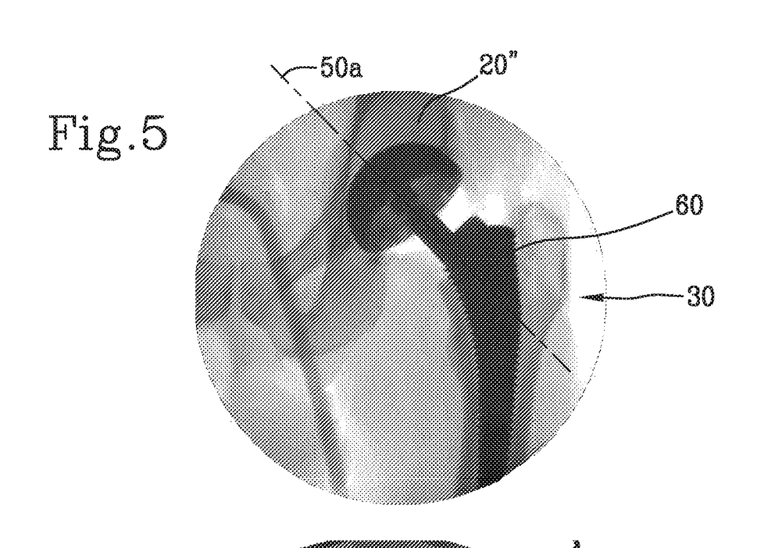
FIG. 5 is a 2D image of the bone structure of the patient's hip and femur in the post-implant configuration.

The system 100 comprises, in addition, a second detecting device 2 adapted to detect at least one 2D image 30 of the pelvic bone 20" in the post-implant situation (FIG. 5). In other words, a series of 2D X-rays are taken of the pelvic and femoral area, preferably with the temporary implant 60 in situ, in order to visualise the pelvic and femoral area after the implant.

The system 100 comprises, in addition, a processing unit 3 configured to acquire and process the 2D image (FIG. 5) and a selected image of the 3D model according to a first inclination.

The processing unit 3, in fact, comprises a selecting module 4' designed to select an image of the 3D model according to a first inclination of the same. In other words, the 3D model is rotated until an image that approximates the post-implant 2D image is obtained.

The processing unit 3 also comprises a first identifying module 4 configured to identify a reference element on the image of the 3D model. This reference element is the acetabular cup 40 (FIG. 9).

The processing unit 3 also comprises a second identifying module 5 configured to identify a plurality of reference points 50 on the 2D image. These reference points 50 are preferably represented by an ellipse given by the projection of the edge of the acetabular cup.

Figure 10:
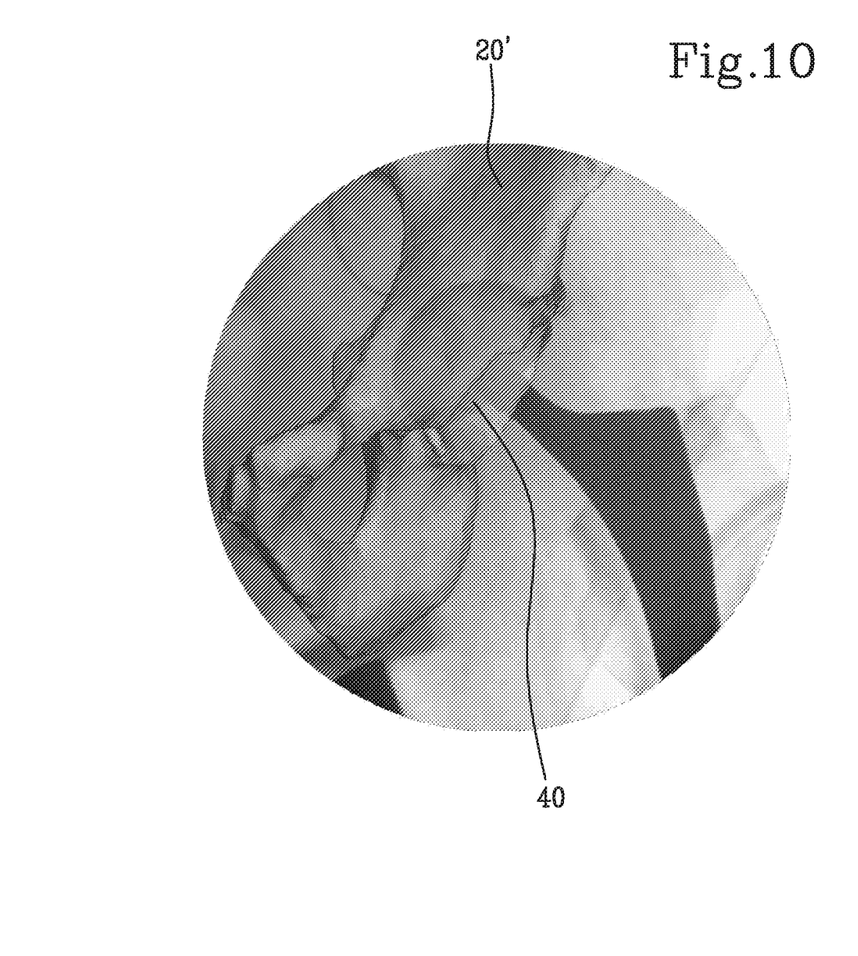
FIG. 10 is the superimposition of the selected 3D image in FIG. 9 with the 2D image in FIG. 5.

A superimposition module 6, included within the processing unit 3, is configured to superimpose the 2D image on the selected image of the 3D model (FIG. 10).

In detail, the superimposition module 6 is configured to receive, from the first 4 and second 5 identifying modules, the 2D and 3D images on which the reference points 50 and the reference element 40 were identified, respectively, and to superimpose the 2D image with the selected image of the 3D model.

The system 100 comprises, in addition, again inside the processing unit 3, a checking module 7 configured to check the correct superimposition and correspondence of the reference points of the 2D image with the reference element of the selected image of the 3D model.

The checking module 7 is configured to receive, from the superimposition module 6, the superimposed 2D and 3D images, and to check the correct superimposition and correspondence of the reference points 40 of the 2D image with the reference element 50 of the selected image of the 3D model.

Figure 11:
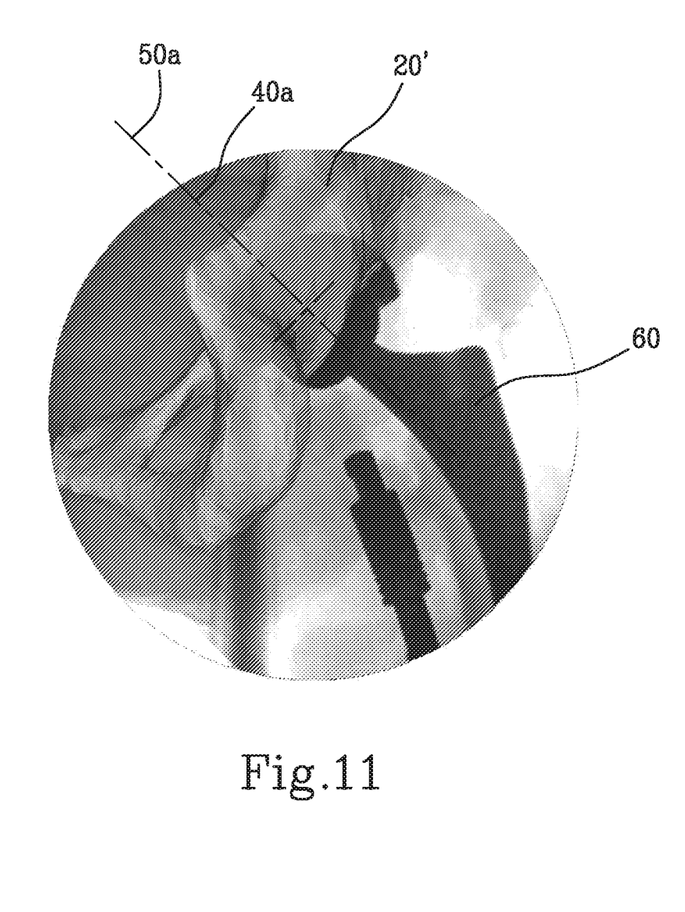
FIG. 11 is the same image as FIG. 10, in which the axes of the acetabular cup, which are visible in the selected image of the 3D model superimposed on the axis passing through the centre defined by the projection of the ellipse of the acetabular cup of the 2D image, are marked.
Figure 12:
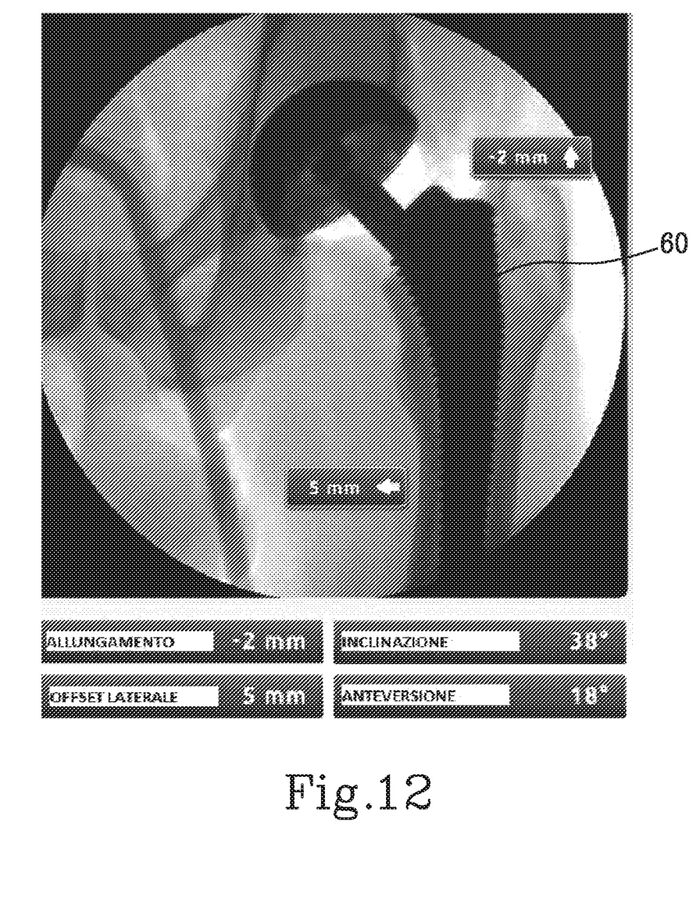
FIG. 12 is an example of a screenshot that returns the characteristic numerical values of lateral offset, leg lengthening, inclination, and anteversion.

In detail, the checking module 7 is configured to check that the alignment and the superimposition between the central symmetry axis 40a of the acetabular cup and the axis 50a passing through the centre of the ellipse, given by the projection of the acetabular cup, is close to a predetermined value of compliance to a predetermined superimposition criterion (FIG. 11).

The processing unit 3 comprises, in addition, a detecting module 9 configured to detect possible differences in the positioning of the pelvic bone in the post-implant configuration with respect to the preoperative situation as a function of the superimposition and correspondence of the reference points of the 2D image with the reference element of the image of the 3D model. In detail, the detecting module 9 is configured to detect the possible anteversion and inclination of the pelvic bone in the post-implant configuration with respect to the preoperative situation as a function of the superimposition and correspondence of the reference points of the 2D image with the reference element of the selected image of the 3D model. In other words, following the superimposition of the 2D image with the selected image of the 3D model, it is possible, as a result of the correct superimposition of the projection of the edge of the acetabular cup in the post-implant position and of the acetabular cup in the preoperative position, respectively, to evaluate the actual degree and value of anteversion and inclination of the cup with respect to the preoperative position.

Finally, the system 100 also comprises within the processing unit 3, a signal 10 generating module 8 configured to generate a signal representative of a value of compliance to a predetermined superimposition criterion between the reference points of the 2D image and the reference element of the image of the 3D model. In other words, a compliance value is predetermined with respect to a predetermined superimposition criterion. If the superimposition of the two images, in particular the superimposition of the acetabular cup of the selected image of the 3D model and the projection of the edge of the ellipse of the acetabular cup of the 2D image do not coincide within a predetermined margin of error, then it is necessary to repeat the procedure, as will be described below and the selected image of the 3D model will have to be modified using the selecting module 4', in order to rotate it to a position that better approximates the 2D image, again in terms of the projection of the edge of the acetabular cup.

In other words, the 3D model is rotated until the edge of the acetabular cup coincides with the ellipse given by the projection of the acetabular cup in 2D with an approximation less than or equal to the predetermined compliance value.

Once the superimposed images coincide within a certain margin of error, then there is the correct superimposition and correspondence of the reference points with the reference element within certain permissible margins of error, for example 1 mm. At this point, a compliance signal representative of this compliance value is returned, as well as the numerical values 11 regarding the anteversion and post-implant acetabular cup inclination with respect to the pre-operative situation.

The latter procedure is actuated by a detecting module 9 that is configured to receive the signal 10, and having detected the possible anteversion and inclination of the acetabular cup in the post-implant configuration with respect to the preoperative situation, to return the numerical values 11 indicative of the post-implant anteversion and inclination of the acetabular cup with respect to the pre-operative configuration.

In detail, the system described so far, to which this invention relates, is used to implement the method obtained by means of a computer to check the correct alignment of a hip prosthesis, to which this invention also relates.

This method of checking involves a first step of checking the offset (or lateral displacement) and leg lengthening parameters, which are evaluated by applying the well-known 2D/2D method.

Figure 2:
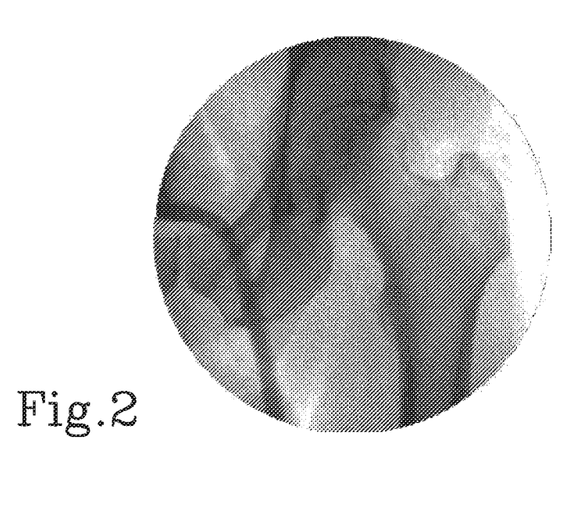
FIG. 2 is a 2D image of the bone structure of the hip and femur in the preoperative condition.
Figure 3:
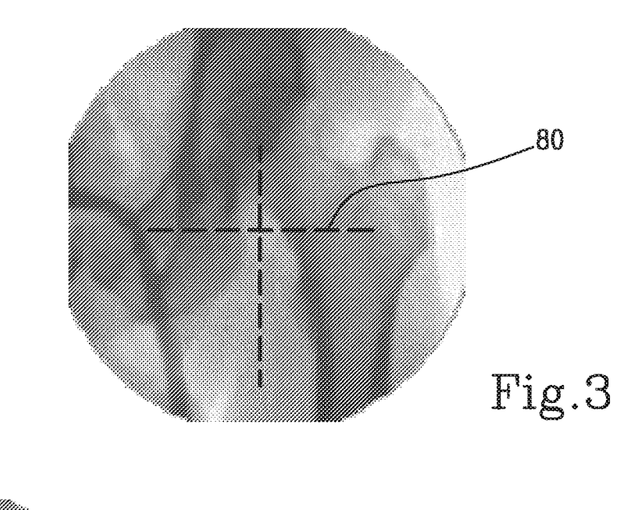
FIG. 3 is the image in FIG. 2 in which the user has marked a horizontal and vertical reference.

Two 2D images are taken: a first preoperative image (FIG. 2), i.e. an image of the patient before surgery and without any kind of implant inside it, and a post-implant image (FIG. 5), after positioning the acetabular cup and femoral stem 60 and providing them to a piece of software. The user first acts on the preoperative image (without implants), choosing an arbitrary reference system 80 (FIG. 3). This reference system 80, consisting of a pair of axes at 90 degrees from each other (a system very similar to Cartesian axes) is chosen by the surgeon and positioned by him/her on the preoperative image of the patient based on his/her experience and by means of appropriate reference points, for example, by aligning one of the axes to the bone construction. In any case, the reference system is chosen based on the surgeon's experience and preferences.

Figure 4:
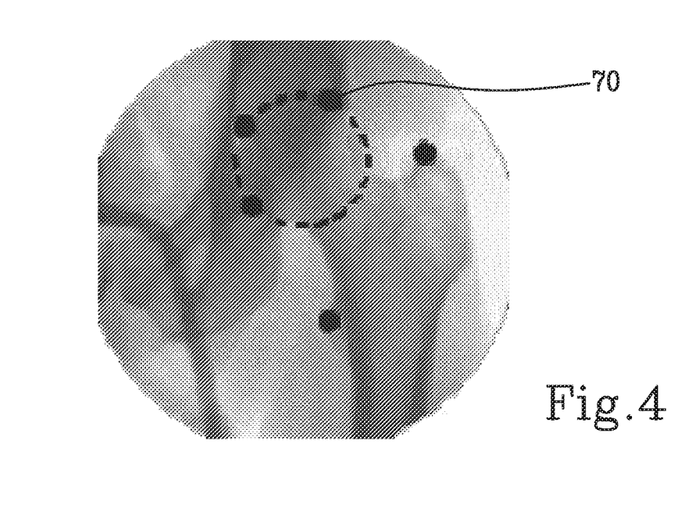
FIG. 4 is the image in FIG. 2 in which reference points have been identified.

There are characteristic points on the image (FIG. 4): centre of rotation of the hip, large trochanter, small trochanter, and "teardrop" (bone formation at the side of the acetabular cup).

The user then moves on to processing the image of the patient with the implants: three points 70 are selected in order to identify the ellipse of the acetabular cup (FIG. 6) (the three points are taken along the edge of the acetabular cup). This identifies the position and size of the acetabular cup. The software checks that the two images are compatible at the scale level; if they are not, it works on the images to make them compatible (thus obtaining the same scale).

At this point, the software divides the preoperative image of the patient into two parts: a portion containing the pelvis and a portion containing the femur.

The images are then superimposed: in the background is the post-implant image of the patient on top of which the preoperative image of the patient will be superimposed.

Figure 7:
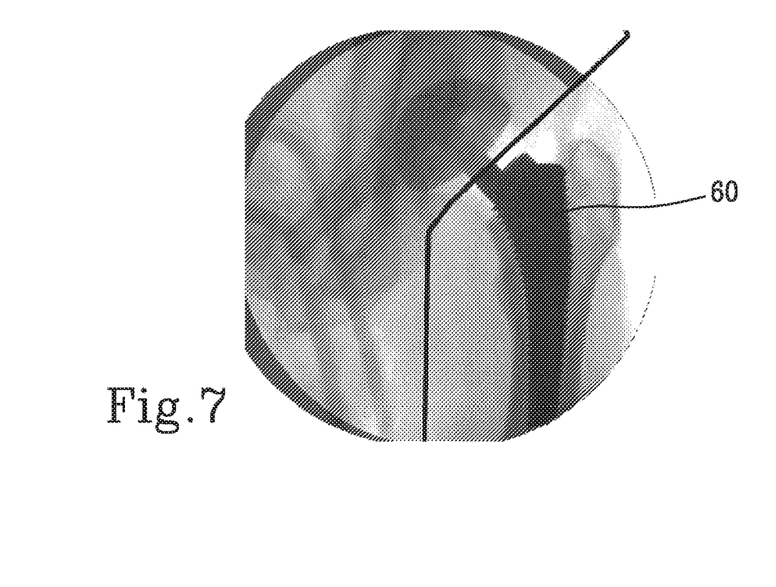
FIG. 7 is the superimposition of the two 2D images in FIG. 2 and FIG. 5, in which the upper part relating to the pelvic bone is aligned.
Figure 8:
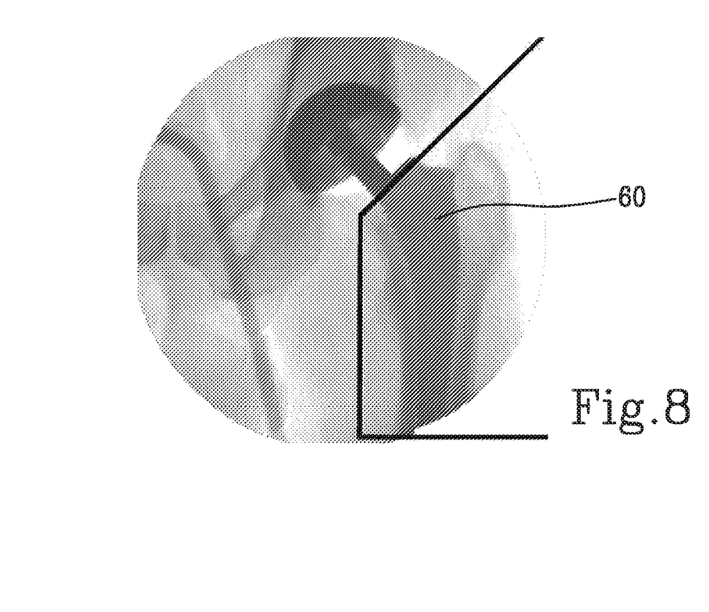
FIG. 8 is the superimposition of the two 2D images in FIG. 2 and FIG. 5, in which the lower part relating to the femur is aligned.

The user first works on the superimposition of the pelvis with the part of the operated patient's image that contains the pelvis (FIG. 7). The right superimposition is found (the software does this step and the surgeon can correct if, visually, not satisfied with the result). Then the user proceeds with the superimposition of the portion of the patient's pre-operative image containing the femur (the software does this step and the surgeon can correct if not satisfied, visually, with the result) (FIG. 8).

At this point, the software calculates the offset, i.e. it checks and calculates how much the images have been translated or rotated to make them match.

To evaluate the anteversion and inclination of the pelvic bone of the post-implant position with respect to the pre-operative one, it is necessary, instead, to apply the method that this invention relates to, called the 2D 3D method, because it uses the superimposition of a 2D image and, suitably, a selected image of the 3D model.

The method comprises the steps of detecting a 3D model of the pelvic bone 20" of a preoperative patient and detecting at least one 2D image of the pelvic bone 20" in a post-implant situation.

The 3D model is detected, preferably, using preoperative tomographies. An initial trial should preferably be performed with a provisional stem and femoral head and then, once it has been ascertained that the positions of the provisional implants correspond to the patient's preoperative anatomy, they should be replaced with the definitive prostheses.

Once the 3D model has been acquired, the model is positioned at a certain inclination and an image of the 3D model at an initial inclination of the model selected.

Figure 6:
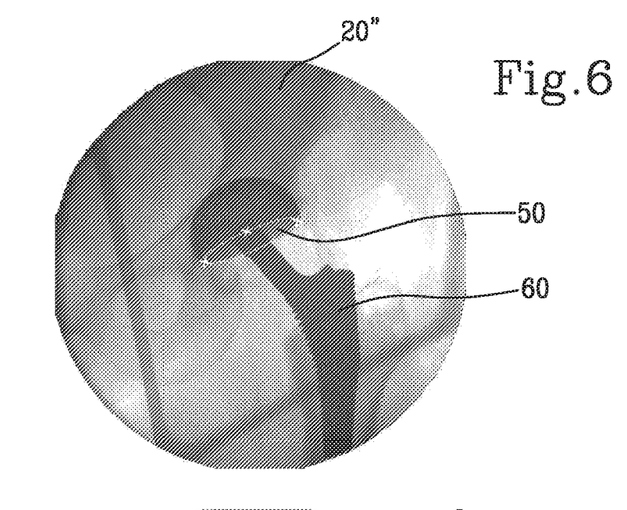
FIG. 6 is the post-implant 2D image on which the user has identified some reference points.

A reference element 40 is then defined and detected on the selected image of the 3D model (FIG. 9). This reference element is, preferably, the acetabular cup. Similarly, a plurality of reference points 50 is identified on the 2D image that are, preferably, represented by the projection of the edge of the ellipse of the acetabular cup (FIG. 6).

The method then involves the step of superimposing the 2D image on the selected image of the 3D model and then checking the correct superimposition and correspondence of the reference points 50 identified on the 2D image with the reference element 40 identified on the image of the 3D model.

In detail, the superimposition of the 2D image and of the image of the 3D model involves aligning the central symmetry axis 40*a* of the acetabular cup with the axis 50*a* passing through the centre of the ellipse given by the projection of the ellipse of the acetabular cup.

The method also involves the step of generating a signal representative of a value of compliance to a predetermined superimposition criterion between the reference points of the 2D image and the reference element of the image of the 3D model.

If said predetermined compliance value is above a predetermined error threshold, the inclination of the 3D model is modified and the procedure repeated.

The predetermined compliance value occurs at the perfect superimposition and correspondence between the acetabular cup of the 3D model and the ellipse given by the 2D projection of the acetabular cup.

When the correct image of the 3D model is identified, then the user can proceed with detecting possible differences in the positioning of the pelvic bone in the post-implant configuration with respect to the preoperative situation as a function of the superimposition and correspondence of the reference points of the 2D image with the reference element of the image of the 3D model.

In detail, any differences in positioning are related to variations in anteversion and inclination of the acetabular cup between the preoperative and post-implant positions.

In other words, it is necessary to evaluate how much the pelvis is rotated around a transverse axis passing through the patient's hips and how much the acetabular cup is rotated (following the insertion of the prosthesis) towards the patient's head or feet.

If any differences in positioning are detected, the relative numerical values 11 are emitted that, when properly compared with the parameters established in the preoperative phase, give the surgeon an indication as to whether the temporary implant is well inserted and correctly positioned or whether its position should be changed before positioning the final prosthesis. In the latter case, the position of the temporary implant is modified and the checking procedure described in both the 2D 2D and 2D 3D parts is repeated.

In other words, a 3D model of the patient's pelvis without implants is thus produced in the preoperative phase. This is done by generating it from the tomographies obtained before the operation. This 3D model reconstructs the characteristics of the patient's bone.

At this point the three-dimensional model of the unoperated bone is superimposed onto the 2D image of the operated patient.

The software automatically searches and finds the position for the superimposition that most closely approximates the previously determined ellipse on the patient's post-implant image to the elliptical shape of the edge of the acetabular cup of the patient's 3D model in the preoperative situation. The software shows this superimposition, which can be modified by the surgeon if necessary. At this point, the software calculates the anteversion and the inclination of the acetabular cup no longer based on an arbitrary reference system given by the surgeon chosen based on his/her experience, but on the patient's real bone model.

This procedure can be done both in the final step the operation, to check that everything has gone well, and during the operating steps themselves. In this second case, in fact, instead of using and implanting the final implants, testers or test implants are used.

Using the temporary implant, if the calculated values go well and reflect what was expected and predefined in the preoperative phase, the surgeon removes the tester and implants the actual acetabular cup. If it does not go well, the surgeon changes the inclination of the tester or its position, takes a second picture, performs the superimposition with the 3D model again, and calculates and checks whether the values are correct like this. If everything matches, and the values obtained are within certain error parameters, then the final prosthesis is implanted.

The invention certainly makes it possible to obtain much more precise and accurate data on the anteversion and inclination values of the acetabular cup because everything is computer-assisted, and the references on which these parameters are evaluated are the patient's own bone references and not references identified manually by the surgeon, and thus already containing errors or inaccuracies.

The invention claimed is:

1. A method obtained by means of computer for checking correct alignment of a hip prosthesis, the method comprising:
   acquiring a 3D model of a pelvic bone of a patient in a preoperative phase;
   detecting at least one 2D image of the pelvic bone in post-implant situation;
   selecting an image of the 3D model according to a first inclination thereof and detecting a reference element, represented by an acetabular cup, on said selected image of the 3D model;
   identifying a plurality of reference points on the 2D image defining an ellipse given by a projection of an edge of the acetabular cup;
   superimposing the 2D image on said selected image of the 3D model;
   checking the correct superimposition and correspondence of the reference points of the 2D image with the reference element with said image of the 3D model;
   generating a signal representative of a value of compliance to a predetermined superimposition criterion between the reference points of the 2D image and the reference element of the selected image of the 3D model;
   if said predetermined compliance value is above a predetermined error threshold, modifying the inclination of the 3D model and repeating the above steps;
   if said predetermined compliance value is below a predetermined error threshold, the image of the 3D model identified is correct and the superimposition and correspondence between the acetabular cup of the 3D model and the ellipse, given by the projection of the acetabular cup in 2D, is perfect, detecting possible differences in the positioning of the pelvic bone in post-implant configuration with respect to the preoperative situation as a function of the superimposition and correspondence of the reference points of the 2D image with the reference element of the image of the 3D model.

2. The method according to claim 1, wherein the superimposition of the image of the 3D model and of the 2D image includes, respectively, aligning a central symmetry axis of the acetabular cup with the axis passing through a center of the ellipse given by the projection of the ellipse of the acetabular cup.

3. The method according to claim 1, comprising the step of modifying the inclination of the 3D model if said predetermined compliance value is above a predetermined error threshold; said compliance value occurring at the perfect superimposition and correspondence between the acetabular cup of the 3D model and the ellipse given by the 2D projection of the acetabular cup.

4. The method according to claim 1, comprising the step of detecting the possible post-implant anteversion and inclination of the acetabular cup with respect to the preoperative situation as a function of the superimposition and correspondence of the reference points of the 2D image with the reference element of the image of the 3D model, and the step of returning numerical values indicative of such rotations of the pelvic bone.

5. The method according to claim 1, wherein the detection of the 3D model of the pelvic bone occurs by means of preoperative fluoroscopies or tomographies.

6. A system for checking correct alignment of a hip prosthesis, comprising:
   a first detecting device adapted to detect a 3D model of a pelvic bone of a patient in a preoperative phase;
   a second detecting device adapted to detect at least one 2D image of the pelvic bone in a post-implant; configuration; and
   a computer-assisted processing unit utilizing software configured to acquire and process the 2D image and a selected image of the 3D model according to a first inclination, wherein the computer-assisted processing unit further utilizes the software to execute steps comprising:
   identifying a reference element on the image of the 3D model;
   identifying a plurality of reference points on the 2D image;
   superimposing the 2D image on the selected image of the 3D model;

checking for correct superimposition and correspondence of the reference points of the 2D image with the reference element of the image of the 3D model;

generating a signal representative of a value of compliance to a predetermined superimposition criterion between the reference points of the 2D image and the reference element of the image of the 3D model; and detecting possible anteversion and inclination of the pelvic bone in the post-implant configuration with respect to the preoperative phase as a function of the superimposing and correspondence of the reference points of the 2D image with the reference element of the selected image of the 3D model.

7. The system according to claim 6, wherein said first detecting device detects a 3D model of the pelvic bone of the patient by means of preoperative fluoroscopies or tomographies.

8. The system according to claim 7, wherein said steps further comprise selecting the selected image of the 3D model according to the first inclination thereof.

9. The system according to claim 8, wherein said reference element is represented by an acetabular cup.

10. The system according to claim 9, wherein said reference points are represented by an ellipse given by a projection of an edge of the acetabular cup.

11. The system according to claim 6, wherein said steps further comprise:

configuring, the 2D and 3D images on which the reference points and the reference element were identified, respectively, and superimposing the 2D image with the selected image of the 3D model.

12. The system according to claim 11, wherein said steps further comprise:

receiving from the computer-assisted processing unit, the superimposed 2D and 3D images, and checking for correct superimposition and correspondence of the reference points of the 2D image with the reference element of the selected image of the 3D model.

13. The system according to claim 12, wherein said steps further comprise checking that alignment between a central symmetry axis of an acetabular cup and an axis passing through a center of an ellipse given by a projection of the acetabular cup is close to a predetermined value of compliance with a predetermined superimposition criterion.

14. The system according to claim 13, wherein said steps further comprise:

receiving, from the computer-assisted processing unit, data related to said predetermined value of compliance and generating a signal representative of said value of compliance if there is correct superimposition and correspondence of the reference points with the reference element.

15. The system according to claim 14, wherein said steps further comprise receiving said signal, and upon detecting anteversion and inclination of the pelvic bone in the post-implant configuration with respect to the preoperative phase has been detected, returning numerical values indicative of post-implant anteversion and inclination of the pelvic bone with respect to the preoperative phase.

* * * * *